United States Patent [19]

Bruza

[11] Patent Number: 4,529,556
[45] Date of Patent: Jul. 16, 1985

[54] BIS((ARYL)VINYL)BENZENES

[75] Inventor: Kenneth J. Bruza, Midland, Mich.

[73] Assignee: The Dow Chemical Company, Midland, Mich.

[21] Appl. No.: 524,710

[22] Filed: Aug. 19, 1983

[51] Int. Cl.³ .................. C07C 12/00; C07C 39/00
[52] U.S. Cl. .................. 260/465 K; 260/465 G; 260/465 E; 260/465 H; 549/218; 549/512; 549/551; 549/553; 564/161; 564/162; 564/164; 564/165; 564/166; 564/169; 564/170; 564/171; 564/176; 564/177; 564/341; 564/342; 564/344; 564/374; 560/11; 560/12; 560/61; 568/716; 568/717; 568/718; 568/720; 568/729; 568/731; 568/763; 568/766
[58] Field of Search .............. 568/717, 718, 720, 729, 568/731, 763, 766, 592, 660, 720; 260/465 K, 568/465 G, 465 E, 465 H; 549/218, 512, 551, 553; 564/166, 169, 170, 171, 176, 177, 341, 342, 344, 564/374; 560/11, 12, 61

[56] References Cited

U.S. PATENT DOCUMENTS

| 2,625,570 | 1/1953 | Pines et al. | 568/716 |
|---|---|---|---|
| 2,865,887 | 12/1958 | Brown | 260/47 |
| 3,026,297 | 3/1962 | Spacht | 260/45.95 |
| 3,232,993 | 2/1966 | Vitrone | 260/619 |
| 3,309,337 | 3/1967 | Hurlock et al. | 568/720 |
| 3,312,657 | 4/1967 | Lund et al. | 260/45.8 |
| 3,378,518 | 4/1968 | Doyle | 260/45.95 |
| 3,755,446 | 8/1973 | Schevermann | 564/156 |
| 3,778,409 | 12/1973 | Oertel et al. | 260/45.8 |
| 3,956,395 | 5/1976 | Meyer | 260/465 K |
| 4,097,515 | 6/1978 | Siegrist et al. | 260/465 G |
| 4,217,301 | 8/1980 | Siegrist et al. | 260/465 K |
| 4,316,860 | 2/1982 | Märky | 260/465 K |
| 4,317,782 | 3/1982 | Eckstein et al. | 260/465 K |
| 4,335,055 | 6/1982 | Blaser et al. | 568/592 |
| 4,380,514 | 4/1983 | Seybold | 260/465 G |
| 4,390,476 | 6/1983 | Marky | 260/465 K |

OTHER PUBLICATIONS

Heck et al., *Journal of Organic Chemistry*, 37(14), 2320 (1972).
Asano et al., *J. Chemical Society, (C), 3691, 1971.*
Shue, *Journal of the American Chemical Society*, 93 (25), 7116 (1971).
Heck, *Journal of the American Chemical Society*, 90 (20), 5535 (1968).
Heck, *Journal of the American Chemical Society*, 90 (20), 5518 (1968).
Fujiwara et al., *Journal of Organic Chemistry*, 41 (10), 1681 (1976).

*Primary Examiner*—John Kight
*Assistant Examiner*—Kriellion Morgan
*Attorney, Agent, or Firm*—Norman L. Sims

[57] ABSTRACT

The invention bis((aryl)vinyl)benzenes wherein the aryl and benzene moieties may be substituted, and the vinyl carbon alpha to the central benzene ring may be further substituted with an aliphatic group.

11 Claims, No Drawings

BIS((ARYL)VINYL)BENZENES

BACKGROUND OF THE INVENTION

This invention relates to novel vinyl-bridged aromatic compounds.

Compounds in which three or more benzene rings are linked by saturated alkylene groups are known. See Oertel et al., U.S. Pat. No. 3,778,409; Doyle, U.S. Pat. No. 3,378,518; Lund et al., U.S. Pat. No. 3,312,657; Vitrone, U.S. Pat. No. 3,232,993; Spacht, U.S. Pat. No. 3,026,297; and MacKenzie, U.S. Pat. No. 2,865,887. Oertel et al., U.S. Pat. No. 3,778,409 discloses that such compounds which contain two hydroxyl groups are useful as in stabilizing polyurethanes against degradation and discoloration under the action of ultraviolet radiation, oxygen, and atmospheric constituents (i.e., nitrogen oxides and heat). Doyle et al., U.S. Pat. No. 3,378,518 discloses that such compounds containing two or more hydroxyl groups are useful in stabilizing polymers prepared from monoolefins from degradation from oxidation, exposure to ultraviolet light and heat. Lund et al., U.S. Pat. No. 3,312,657 discloses that such hydroxyl-containing compounds are useful in stabilizing polymers prepared from halogen-containing olefins.

Spacht, U.S. Pat. No. 3,026,297 discloses that such hydroxyl-containing compounds are useful in stabilizing rubber compositions.

Although the compounds described hereinbefore are relatively air stable and ultraviolet radiation stable, such compounds will undergo degradation when exposed to such conditions for prolonged periods of time.

What are needed are compounds which exhibit increased stability when exposed to ultraviolet light and air. What are further desirable are compounds which act as ultraviolet light sensitizers or exhibit fluorescing properties.

SUMMARY OF THE INVENTION

The invention involves bis((aryl)vinyl)benzenes wherein the aryl and benzene moieties may be substituted and the vinyl carbon alpha to the central benzene ring may be substituted with an aliphatic group.

Another aspect of this invention is a process for the preparation of bis((phenyl)vinyl)benzenes which comprises contacting a substituted or unsubstituted dialkenyl benzene with a substituted or unsubstituted halobenzene in the presence of a catalytic amount of a palladium, iridium, rhodium, ruthenium, platinum, nickel, cobalt, or osmium, under conditions such that a bis((phenyl)vinyl)benzene is prepared.

In a further aspect, this invention relates to polyepoxides which are the reaction products of vicinal epoxides or vicinal epoxide-containing compounds with the bis((aryl)vinyl)benzenes of this invention.

The bis((aryl)vinyl)benzenes of this invention demonstrate surprising stability to exposure to air and ultraviolet radiation. Further, such compounds are fluorescent and exhibit ultraviolet sensitivity.

The bis((aryl)vinyl)benzenes of this invention are useful as dyes, ultraviolet light sensitizers and fluorescing agents. These compounds are useful in the preparation of epoxy resins. The compounds are further useful as antioxidants and ultraviolet light stabilizers in various polymeric compositions, for example, polyvinyl chlorides and polyurethanes.

DETAILED DESCRIPTION OF THE INVENTION

The bis((aryl)vinyl)benzenes of this invention can be substituted on the aryl or benzene moieties with a hydroxy, glycidyl, carbamoyl, formyl, nitro, cyano, amino, epoxy, carboxyl, mercapto, hydrocarbyloxy, hydrocarbanoyloxy, hydrocarbyloxycarbonyl, hydrocarbyl carboxamido, hydrocarbylthio, hydrocarbyl sulfinyl, hydrocarbyl sulfonyl, trialkylphosphorus, hydrocarbyl, or hydrocarbyl substituted with a hydroxy, glycidyl, epoxy, carbamoyl, formyl, nitro, cyano, amino, carboxyl, mercapto, hydrocarbyloxy, hydrocarbanoyloxy, hydrocarbyloxycarbonyl, hydrocarbyl carboxamido, hydrocarbylthio, hydrocarbyl sulfinyl, or hydrocarbyl sulfonyl.

The bis((aryl)vinyl)benzenes of this invention are preferably those which correspond to the formula

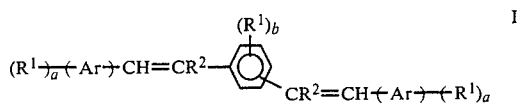

wherein
Ar is an arylene group;
$R^1$ is separately in each occurrence hydrogen, hydroxy, glycidyl, epoxy, carbamoyl, formyl, nitro, cyano, amino, carboxyl, mercapto, hydrocarbyloxy, hydrocarbanoyloxy, hydrocarbyloxycarbonyl, hydrocarbyl carboxamido, hydrocarbylthio, hydrocarbyl sulfinyl, hydrocarbyl sulfonyl, hydrocarbyl or hydrocarbyl substituted with a hydroxy, glycidyl, epoxy, carbamoyl, formyl, nitro, cyano, amino, carboxyl, mercapto, hydrocarbyloxy, hydrocarbanoyloxy, hydrocarbyloxycarbonyl, hydrocarbyl carboxamido, hydrocarbylthio, hydrocarbyl sulfinyl, or hydrocarbyl sulfonyl group;
$R^2$ is a hydrogen or hydrocarbyl group;
a is separately in each occurrence an integer of from 1 to 5; and
b is an integer of 0 to 4.

Hydrocarbyl means herein an organic radical containing carbon and hydrogen atoms. The term hydrocarbyl includes the following organic radicals: alkyl, alkenyl, alkynyl, cycloalkyl, cycloalkenyl, aryl, aliphatic, cycloaliphatic, aralkyl and alkaryl. Aliphatic refers herein to straight- and branched-, and saturated and unsaturated, hydrocarbon chains, that is, alkyl, alkenyl or alkynyl. Cycloaliphatic refers herein to saturated and unsaturated cyclic hydrocarbons, that is, cycloalkenyl and cycloalkyl. The term aryl refers herein to biaryl, biphenylyl, phenyl, naphthyl, phenanthranyl, anthranyl and two aryl groups bridged by an alkylene group. Alkaryl refers herein to an alkyl-, alkenyl- or alkynyl-substituted aryl substituent wherein aryl is as defined hereinbefore. Arylene refers herein to a divalent aromatic moiety. Aralkyl means herein an alkyl, alkenyl or alkynyl group substituted with an aryl group, wherein aryl is as defined hereinbefore. Alkyl includes straight-and branched-chain methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl and eicosyl groups.

Cycloalkyl refers to alkyl groups containing one, two, three or more cyclic rings. Cycloalkenyl refers to mono-, di- and polycyclic groups containing one or more double bonds.

Hydrocarbyloxy means herein a hydrocarbyl group which is further bonded to an oxygen so as to form an ether substituent. Hydrocarbonyloxy means herein a hydrocarbyl group bonded to a carbonyl group, which is further bonded to an oxygen

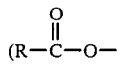

wherein R is a hydrocarbyl group). Hydrocarbyloxycarbonyl means herein a hydrocarbyl group bonded to an oxygen which is further bonded to a carbonyl group, so as to form an ester

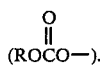

Hydrocarbyl carboxamido means herein a hydrocarbyl group bonded to a carbonyl group which is further bonded to a nitrogen

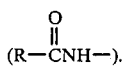

Hydrocarbylthio means herein a hydrocarbyl group bonded to a sulfur atom, to form a thioether (R—S—). Hydrocarbyl sulfinyl means herein a hydrocarbyl group bonded to a sulfur atom which is further double bonded to an oxygen atom

Hydrocarbyl sulfonyl means herein a hydrocarbyl group bonded to a sulfur atom which is further double bonded to two oxygen atoms

In formula I, Ar is preferably phenylene. $R^1$ is preferably hydrogen, hydroxy, nitro, glycidyl, epoxy, carbamoyl, formyl, cyano, amino, carboxyl, mercapto, $C_{1-20}$ hydrocarbyloxy, $C_{1-20}$ hydrocarbanoyloxy, $C_{1-20}$ hydrocarbyloxycarbonyl, $C_{1-20}$ hydrocarbyl carboxamido, $C_{1-20}$ hydrocarbylthio, $C_{1-20}$ hydrocarbyl sulfinyl, $C_{1-20}$ hydrocarbyl sulfonyl, $C_{1-20}$ hydrocarbyl or $C_{1-20}$ hydrocarbyl substituted with a hydroxy, glycidyl, epoxy, carbamoyl, formyl, nitro, cyano, amino, carboxyl, mercato, $C_{1-20}$ hydrocarbyloxy, $C_{1-20}$ hydrocarbanoyloxy, $C_{1-20}$ hydrocarbyloxycarbonyl, $C_{1-20}$ hydrocarbyl carboxamido, $C_{1-20}$ hydrocarbylthio, $C_{1-20}$ hydrocarbyl sulfinyl or $C_{1-20}$ hydrocarbyl sulfonyl group. $R^1$ is more preferably hydrogen, hydroxyl, glycidyl, nitro, formyl, carboxyl, $C_{1-20}$ alkyl, $C_{1-20}$ aryl, or $C_{1-20}$ alkyl or aryl substituted with a hydroxyl, nitro, glycidyl, formyl or carboxyl group. $R^1$ is even more preferably hydrogen, hydroxide, carboxyl, formyl, or $C_{1-10}$ alkyl or aryl substituted with a hydroxy, nitro, carboxyl, formyl or glycidyl group. $R^1$ is most preferably hydroxy, nitro or acetoxy.

$R^2$ is preferably hydrogen or $C_{1-20}$ aliphatic, more preferably hydrogen or $C_{1-20}$ alkyl, even more preferably hydrogen or $C_{1-10}$ alkyl, and most preferably hydrogen. Preferably, a is 1. Preferably, b is 0.

Among preferred embodiments of this invention are bis((4-hydroxyphenyl)vinyl)benzene, bis((4-acetoxyphenyl)vinyl)benzene, bis((4-nitrophenyl)vinyl)-benzene, bis((phenyl)vinyl)benzene, bis((4-acetylaminophenyl)vinyl)benzene.

Of the potential isomeric forms of this invention, the para isomers are preferred.

The bis((aryl)vinyl)benzenes of this invention are prepared by contacting an aryl halide with a divinylbenzene in the presence of the catalysts described hereinafter.

The aryl halides which are used in this invention include those which correspond to the formula

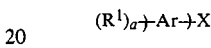

wherein Ar, $R^1$ and a are as defined hereinbefore, and X is chlorine, bromine or iodine. X is preferably bromine or iodine, and most preferably bromine.

The divinylbenzenes which are useful for preparing the compounds of this invention include those which correspond to the formula

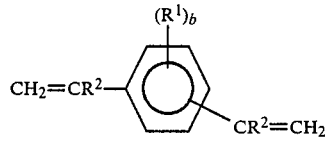

wherein $R^1$, $R^2$ and b are as defined hereinbefore.

The aryl halides and divinylbenzenes can be reacted in any molar ratio in which bis((aryl)vinyl)benzene is prepared. Generally at least two moles of aryl halide are required for each mole of divinylbenzene. The use of slight excess over the stoichiometric ratio of aryl halide to divinyl benzene results in optimum yields of product, for example a molar ratio of 2.10 to 1.

The aryl halide and divinylbenzene are reacted in the presence of a catalytic amount of palladium, iridium, rhodium, ruthenium, platinum, nickel, cobalt or osmium. It is preferred to use such metals in the zero valent state. Preferred metals are palladium and platinum with palladium most preferred. The catalyst is preferably used in the presence of a trihydrocarbyl phosphine co-catalyst which corresponds to the formula $P(R^3)_3$ wherein $R^3$ is a hydrocarbyl radical. $R^3$ is preferably alkyl or aryl, more preferably aryl and most preferably phenyl or tolyl.

It is believed the catalytic species is a complex of the metal catalyst with the trihydrocarbyl phosphine. The catalyst is prepared by contacting a palladium, iridium, rhodium, ruthenium, platinum, nickel, cobalt or osmium salt with a trihydrocarbyl phosphine in a suitable solvent. Suitable solvents include polar organic solvents.

Any salt of the hereinbefore named metals which is soluble in a polar organic solvent can be used to prepare the complex. Examples of salts of the hereinbefore named metals which are suitable in the preparation of the catalyst complex include acetates, hydroxides, halides, carbonates and the like.

Generally the metal salts and the trihydrocarbyl phosphines are contacted under the reaction conditions at which the bis((aryl)vinyl)benzenes are prepared. Under such conditions the complex is prepared.

A catalytic amount of the metal catalyst is between about 0.1 and 100 mole percent based on the aryl halide, preferably between 0.5 and 5 mole percent. The cocatalyst is generally used in molar ratios to the metal salt of between about 1:1 and 10:1, preferably between about 2:1 and 4:1, most preferably between 2:1 and 3:1.

It is advantageous to run the reaction in the presence of a tertiary amine, for example, tri-n-butyl-amine, tri-n-propylamine, triethylamine and the like. The amines act as acid acceptors in that they form salts with the hydrogen halides formed during the reaction.

The reaction is preferably run in a solvent. Suitable solvents are polar organic solvents. Desirable solvents are aromatic hydrocarbons such as toluene, benzene, ethylbenzene and the like; cyclic ethers such as tetrahydrofuran and the like; nitriles such as acetonitrile and the like; and amides such as dimethylformamide. Preferred solvents include toluene, dimethyl formamide, tetrahydrofuran and acetonitrile.

Any temperature at which product is prepared is suitable for this reaction. Desirable temperatures are between 40° C. and 140° C. Below 40° C. the reaction rate is very slow, whereas above 140° C. the catalyst undergoes decomposition and the aryl halides undergo coupling reactions. The preferred temperatures are between about 80° C. 110° C.

Any reaction time which gives the desired yield is suitable. Desirable reaction times are between about 1 and 24 hours. This reaction is usually run at atmospheric pressure, although superatmospheric pressures can also be used.

One preferred embodiment involves the bis((hydroxyaryl)vinyl)benzene. It is preferable that this species be prepared by the reaction of the acetoxyaryl halide with divinylbenzene to prepare the bis((acetoxyaryl)vinyl)benzene. This product can be converted to the bis((hydroxyaryl)vinyl)benzene by treatment with base, for example, an alkali metal hydroxide or carbonate. The use of this process results in a higher yield of purer bis((hydroxyaryl)vinyl)benzene than can be prepared by starting with the hydroxyaryl halide.

The compounds of this invention are stable in the presence of air for long perdiods of time. Such compounds are also stable to prolonged exposure to ultraviolet light. The compounds are also fluorescent.

These compounds are generally useful as fluorescing agents, dyes and ultraviolet sensitizers. Some of the compounds of this invention are useful as monomers and stabilizing agents in polymeric resins, epoxy resins, polyolefins, rubbers, polyhaloolefins and polyurethanes. The use for which a particular compound within the scope of this invention is suitable depends upon the nature of $R^1$.

In one aspect this invention is a polyepoxide which comprises the reaction product of (a) a bis((aryl)-vinyl)benzene wherein the aryl moieties are substituted with an active hydrogen-containing substituent, and (b) a vicinal epoxide. Such polyepoxide may further comprise an active hydrogen-containing compound.

In another aspect the invention is a cured epoxy resin which comprises the reaction product of (a) a bis((aryl)vinyl)benzene wherein the aryl moieties are substituted with an active hydrogen-containing moiety, (b) a polyepoxide, and (c) a curing agent.

These cured epoxy resins may further comprise an active hydrogen-containing compound. Active hydrogen-containing moiety means herein a radical which contains a hydrogen bonded to oxygen, sulfur or nitrogen, for example, OH, $NH_2$, COOH, SH or $CONH_2$. An active hydrogen-containing compound is a compound which has a reactive hydrogen-containing moiety.

The polyepoxides are prepared by contacting a vicinal epoxide with a bis((aryl)vinyl)benzene under conditions such that a polyepoxide is formed. Such processes are well-known in the art. Generally, the vicinal epoxide and bis((aryl)vinyl)benzene are reacted in molar ratios of between 1:1 and 200:1, more preferably between 4:1 and 10:1. In the embodiment wherein the polyepoxides further comprise active hydrogen-containing compounds, the molar ratio of the vicinal epoxide to the sum of the bis((aryl)vinyl)benzene and the active hydrogen-containing compounds is between 1:1 and 200:1, preferably 2:1 to 100:1. The ratio of the bis((aryl)vinyl)benzene to the active hydrogen compound is between about 1:1 and 200:1, preferably between about 1:1 and 100:1.

The cured epoxy resins are prepared by reacting a polyepoxide with a bis((aryl)vinyl)benzene compound with active hydrogen-containing substituents on the aryl moieties, and a curing agent under conditions such that a cured epoxy resin is prepared. Such conditions are generally well-known in the art. In general, the cured epoxy resins comprise between about 50 and 90 percent polyepoxide, between about 0.5 and 100 percent of a bis((aryl)vinyl)benzene, and between about 10 and 20 percent of a curing agent. The cured epoxy resin preferably comprises between about 80 and 90 percent of a polyepoxide, between about 0.5 and 20 percent of a bis((aryl)vinyl)benzene and between about 10 and 20 percent of a curing agent. In the embodiment wherein the cured epoxy resin further comprises an active hydrogen compound, such resin comprises between about 80 and 90 percent of a polyepoxide, between about 0.5 and 100 percent of a bis((aryl)vinyl)benzene, between about 1.0 and 99 percent of an active hydrogen-containing compound, and between about 2 and 20 percent of a curing agent. Preferably the cured epoxy resin comprises between about 70 and 90 percent of a polyepoxide, between about 0.5 and 20 percent of a bis((aryl)vinyl)benzene, between about 1.0 and 50 percent of an active hydrogen-containing compound and between about 10 and 15 percent of a curing agent.

Suitable vicinal epoxides for use in this invention are well-known in the art and include those described in U.S. Pat. No. 4,354,015 (incorporated herein by reference). Examples of such compounds are the alkylene oxides of from 2 to 24 carbon atoms, the epihalohydrins and the polyepoxides.

Suitable polyepoxides useful in this invention are those well-known in the art and include those described in U.S. Pat. No. 4,354,015 and U.S. Pat. No. 4,264,748 (incorporated herein by reference). Included among such polyepoxides described are the glycidyl polyethers of polyhydric phenols and glycidyl ethers of novolac resins.

Reaction conditions for the preparation of the polyepoxides are well-known in the art and include those described in U.S. Pat. Nos. 3,372,142 and 4,354,015 (incorporated herein by reference).

Reaction conditions for the preparation of the cured epoxy resins of this invention are well-known in the art and include those described in U.S. Pat. No. 3,578,616 and U.S. Pat. No. 4,354,015 (incorporated herein by reference). Suitable curing agents are well-known in the art and include those described in U.S. Pat. Nos. 3,578,616 and 3,406,150.

The desirable high temperature properties of these resins are obtained when they are cross-linked to a thermoset material with an aliphatic or aromatic polyamine or an aromatic anhydride, although any of the other common curing agents for polyepoxides can be used when optimum high temperature properties are not required. Aromatic amines which can be used are methylene dianiline, metaphenylene diamine and diamino diphenyl sulfone. Typical aliphatic amines include diethyltriamine, triethylene-tetramine, tetraethylenepentamine, aminoethylpiperazine. Suitable anhydrides for resins having good properties at high temperatures are phthalic anhydride, hexahydrophthalic anhydride, hexachloroendomethylene tetrahydrophthalic anhydride, the maleic anhydride adduct of methyl cyclopentadiene, and others will be well-known.

The active hydrogen compounds useful in this invention are well-known in the art and include those described in U.S. Pat. No. 4,390,645 (incorporated herein by reference).

The polyepoxides of this invention have improved stability to prolonged exposure to air and ultraviolet radiation. Such resins have fluorescent properties. Further, the resins are more rigid than prior art resins. Furthermore, the resins' ultraviolet light sensitivity allows the use of ultraviolet light to monitor the amount of the bis((aryl)vinyl)benzene in the resin.

SPECIFIC EMBODIMENTS

The following examples are presented to further illustrate the invention and do not limit the scope of the invention or claims. All parts and percentages are by weight unless otherwise specified.

EXAMPLE 1

Preparation of 1,4-bis((4-nitrophenyl)vinyl)benzene

Into a 25-ml 3-neck flask, equipped with a nitrogen inlet, reflux condenser, two glass stoppers and a magnetic stirring bar, is placed 2.33 g of a 55.7 percent mixture of divinylbenzene (1.3 g, 10 mmoles). To this is added 5.1 g (20.5 mmoles) of 1-iodo-4-nitrobenzene, 3.89 g (21 mmoles) of tri-n-butylamine, 0.045 g (0.20 mmole) of palladium acetate and 4.0 ml of acetonitrile. This vigorously stirring mixture is heated at reflux for a period of 48 hours. Upon cooling to room temperature, the reaction mixture becomes a solid. The solid is transferred to a beaker containing 100 ml of 10 percent hydrochloric acid with vigorous stirring. The liquid is decanted away and the solid is taken up in ethanol and heated to boiling. Upon cooling, a substance oils out. The ethanol is removed in vacuo and the resulting red brown oil is subjected to column chromatography (silica gel, ethylacetate/n-hexane 1:9). Four major components are isolated and their nuclear magnetic resonance spectra recorded. Low resolution mass spectrometry indicates that the four products are 1,4-bis((4-nitrophenyl)vinyl)benzene (m/e=372), 4-nitro-4-ethylstilbene (m/e=253), 4-nitro-4-vinylstilbene (m/e=251) and 4,4-dinitrostilbene (m/e=244).

EXAMPLE 2

Preparation of bis((4-acetoxyphenyl)vinyl)benzene

Into a 1-liter, 3-neck flask equipped with a magnetic stirring bar, reflux condenser, thermometer and a glass stopper, is placed 56.95 g (0.438 mole) of 95 percent divinylbenzene. To this is added 188.36 g (0.876 mole) of 4-acetoxybromobenzene, 0.981 g (4.38 mmoles) of palladium acetate, 4.0 g (13.14 mmoles) of tri-o-tolylphosphine, 163.2 g (0.88 mole) of tri-n-butylamine and 300 ml of acetonitrile. This vigorously stirred reaction mixture is heated at reflux for a period of 24 hours. The reaction mixture is cooled to room temperature and poured into 1 liter of 10 percent hydrochloric acid with vigorous stirring. The solid is isolated by suction filtration and washed with distilled water, before drying in air. This grey-green solid is treated with 1 liter of toluene, heated to boiling and filtered by gravity. The toluene solution upon cooling begins to deposit a white solid. Suction filtration provides 35 g of the meta isomer of the product. Nuclear magnetic resonance, infrared and elemental analysis are done on the product. The melting point is 206° C.–209° C. C is calculated at 78.4 and 78.6 is found; H is calculated at 5.53 and 5.69 is found. The yield is 35 g, that is, 20 percent.

The solid which is not soluble in hot toluene is taken up in 500 ml of dimethylformamide, heated to boiling and filtered. Upon cooling to room temperature the fluorescent solution begins to deposit a fine, yellow green solid. 60.5 g of this material is obtained which is the para isomer. The nuclear magnetic resonance and infrared are recorded. The melting point is 298° C.––302° C. The yield is 60.5 g, that is, 38 percent. The total yield is 58 percent.

EXAMPLE 3

Preparation of 1,3-bis((4-hydroxyphenyl)vinyl)benzene

Into a 1-liter one-neck flask equipped with a magnetic stirring bar and a reflux condenser is placed a solution of 17.1 g (0.427 mole) of sodium hydroxide in 500 ml of distilled water. To this is added 34 g (0.0854 mole) of 1,3-bis((4-acetoxyphenyl)vinyl)benzene in several portions. The stirring mixture is heated to reflux and maintained at this temperature for 24 hours. The reaction mixture is cooled in an ice bath and treated with 10 percent hydrogen chloride until a pH of 2 is obtained. The lime green solid is isolated by suction filtration and then taken up in 600 ml of distilled water and heated to boiling. The white solid is isolated by suction filtration and washed with 1 liter of boiling water (water washes are neutral). The product is air dried for several hours and then dried in a vacuum oven at 60° C. for 10 hours. The infrared of the product is recorded. The melting point is 232° C.–234° C. The yield is 25.1 g, that is, 94 percent.

EXAMPLE 4

Preparation of cured epoxy resin containing 10 mole percent of 1,4-bis((4-hydroxyphenyl)vinyl)benzene Into a 500-ml resin kettle containing a reflux condenser, thermometer, overhead stirrer with a steel stirring shaft and paddle and a nitrogen inlet tube is placed 86.4 g (0.2541 mole) of a polyepoxide prepared from bisphenol A and epichlorohydrin with an epoxy equivalent weight of 331, 33.86 g (0.1485 mole) of para-bisphenol A and 5.181 g (0.0165 mole) of 1,4-bis((4-hydroxyphenyl)vinyl)benzene. With the system under a nitrogen atmosphere, the reactants are heated to 50° C. with stirring. At this point, 125 mg of A-1 catalyst are added. The reaction is heated to 150° C. (at 145° C., the reaction becomes a homogeneous solution). The reaction begins to exotherm and the external heating is ceased. The temperature eventually reaches 200° C. The reaction is allowed to cool to a temperature of 150° C. where it now is a viscous yellow solution. After 1.5 hours from the first addition of A-1 catalyst, a second 125 mg of catalyst is added and the temperature is maintained at 150° C. for 3 hours. Heating is stopped at this time and the thick solution is poured onto a sheet of aluminum foil and rapidly cooled. The resulting solid is ground to a fine off-white powder. The cured epoxy resin weighs 81.4 g and has an epoxy equivalent weight of 987, a percent epoxy of 4.36 and an epoxy oxygen weight percent of 1.62.

EXAMPLE 5

Preparation of cured epoxy resin containing 20 mole percent of 1,4-bis((4-hydroxyphenyl)vinyl)benzene A cured epoxy resin containing about 20 mole percent of 1,4-bis((4-hydroxyphenyl)vinyl)benzene is prepared by the process described in Example 4. The cured epoxy resin has an epoxy equivalent weight of 991, a percent epoxy of 4.34 and an epoxy oxygen weight percent of 1.62.

EXAMPLE 6

Preparation of films from cured epoxy resins of Examples 4 and 5

The cured epoxy resins of Examples 4 and 5 are made into a 60 percent solution in ethylene glycol n-butyl ether. These solutions are in turn treated in the following fashion: 85 parts of cured epoxy resin in ethylene glycol n-butyl ether, 15 parts of hexamethoxymethyl melamine and 0.5 percent of 40 percent para-toluenesulfonic acid in isopropanol as a catalyst. These formulations are cast as approximately 1-mm thick films on cold rolled steel and Bonderite ® 37. The films are cured at 177° C. for 30 minutes in a forced air oven and then aged for 85 hours. The cured epoxy resins so prepared are tested for reverse impact, solvent resistivity, hardness, blush and adhesive properties. The results are compiled in Table I.

TABLE I

| Example | Epoxy Resin Substrate | Pencil Hardness | Blush | % Adhesion Loss |
|---|---|---|---|---|
| 1* | steel | 8H | slight chalk | 10% dry 100% H$_2$O |
|  | Bonderite | >8H | none | ~2% dry ~2% H$_2$O |
| 2* | steel | >8H | slight chalk | 25% dry 100% H$_2$O |
|  | Bonderite | >8H | none | 0% dry 0% H$_2$O |

*Reverse impact for both examples was <4 in-lb, MEK resistivity was passing and minutes to fail was >30.

The cured epoxy resins prepared from the novel bis((aryl)vinyl)benzene demonstrate good film-forming properties. These films also demonstrate good fluorescent properties.

What is claimed is:

1. Bis((aryl)vinyl)benzenes wherein the aryl moieties are substituted with an hydroxy, epoxy or glycidyl moiety; the benzene moieties may be substituted; and the vinyl carbon alpha to the central benzene ring may be further substituted with an aliphatic group.

2. The bis((aryl)vinyl)benzenes of claim 1 wherein the benzene moieties may be substituted with a hydroxy, glycidyl, carbamoyl, formyl, nitro, cyano, amino, epoxy, carboxyl, mercapto, hydrocarbyloxy, hydrocarbanoyloxy, hydrocarbyloxycarbonyl, hydrocarbyl carboxamido, hydrocarbylthio, hydrocarbyl sulfinyl, hydrocarbyl sulfonyl, trialkylphosphorus, hydrocarbyl, or hydrocarbyl substituted with a hydroxy, glycidyl, epoxy, carbamoyl, formyl, nitro, cyano, amino, carboxyl, mercapto, hydrocarbyloxy, hydrocarbanoyloxy, hydrocarbyloxycarbonyl, hydrocarbyl carboxamido, hydrocarbylthio, hydrocarbyl sulfinyl, or hydrocarbyl sulfonyl.

3. The bis((aryl)vinyl)benzenes of claim 1 which correspond to the formula

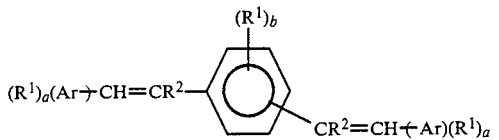

wherein
Ar is an arylene group;
R$^1$ is separately in each occurrence hydroxy, glycidyl, or epoxy group;
R$^2$ is a hydrogen or hydrocarbyl group;
a is separately in each occurrence an integer of from 1 to 5; and
b is separately in each occurrence an integer of 0 to 4.

4. The bis((aryl)vinyl)benzenes of claim 3 wherein R$^1$ is hydroxy.

5. The bis((aryl)vinyl)benzenes of claim 3 wherein R$^2$ is hydrogen or C$_{1-20}$ aliphatic.

6. The bis((aryl)vinyl)benzenes of claim 3 wherein R$^2$ is hydrogen or C$_{1-20}$ alkyl.

7. The bis((aryl)vinyl)benzenes of claim 3 wherein R$^2$ is hydrogen or C$_{1-10}$ alkyl.

8. The bis((aryl)vinyl)benzenes of claim 3 wherein R$^2$ is hydrogen.

9. The bis((aryl)vinyl)benzenes of claim 3 wherein the (aryl)vinyl substituents are in the para position.

10. The bis((aryl)vinyl)benzenes of claim 3 wherein Ar is phenylene.

11. The bis((aryl)vinyl)benzenes of claim 3 wherein a is 1 and b is 0.

* * * * *